(12) United States Patent
March

(10) Patent No.: US 8,455,478 B2
(45) Date of Patent: Jun. 4, 2013

(54) RAPID ONSET LIQUID MIDAZOLAM COMPOSITION FOR BUCCAL ADMINISTRATION

(75) Inventor: Graham Alan March, Surrey (GB)

(73) Assignee: Special Products, Ltd., Weybridge, Surrey (GB)

( * ) Notice: Subject to any disclaimer, the term of this patent is extended or adjusted under 35 U.S.C. 154(b) by 0 days.

(21) Appl. No.: 13/164,922

(22) Filed: Jun. 21, 2011

(65) Prior Publication Data

US 2012/0022051 A1      Jan. 26, 2012

(30) Foreign Application Priority Data

Jun. 22, 2010   (GB) .................................. 1010453.7

(51) Int. Cl.
*A61K 31/55* (2006.01)
*A61K 31/41* (2006.01)

(52) U.S. Cl.
USPC .......................................... 514/219; 514/359

(58) Field of Classification Search
USPC ................................................. 514/219, 359
See application file for complete search history.

(56) References Cited

U.S. PATENT DOCUMENTS

| | | | |
|---|---|---|---|
| 8,217,033 B2 * | 7/2012 | Gizurarson | ................... 514/220 |
| 2005/0153956 A1 | 7/2005 | Mercus | |
| 2008/0070904 A1 * | 3/2008 | Jamieson et al. | ............ 514/220 |

FOREIGN PATENT DOCUMENTS

| | | |
|---|---|---|
| WO | WO 0130391 | 5/2001 |
| WO | WO 03004015 | 1/2003 |
| WO | WO 2005067893 | 7/2005 |
| WO | WO 2008089426 | 7/2008 |
| WO | WO 2009121039 | 10/2009 |

OTHER PUBLICATIONS

Oliver et al., "In situ absorption of midazolam in rats", International Journal of Pharmaceutics 213 (2001) pp. 187-192.
Riitta Andersin, "Solubility and acid-base behaviour of midazolam in media of different pH, studied by ultraviolet spectrophotometry with multicomponent software," Journal of Pharmaceutics & Biomedical Analysis, vol. 9, No. 6, pp. 451-455, 1991.
"Midazolam Hydrochloride 1-mg/ml Oral Liquid", International Journal of Pharmaceutical Compounding, vol. 10, No. 5, Sep. 1, 2006.
Shayne Cox Gad, Pharmaceutical Manufacturing Handbook, Production and Processes, Aug. 2007.
International Search Report in PCT/GB2011/051146 application dated Sep. 27, 2011.
Office Communication on GB 1010453.7 application, dated Oct. 19, 2010.
Office Communication on GB 1010453.7 application, dated Feb. 10, 2011.
Office Communication on GB 1010453.7 application, dated Mar. 11, 2011.

* cited by examiner

*Primary Examiner* — Renee Claytor

(57) ABSTRACT

This application discloses liquid compositions for administration to a patient comprising midazolam and a pharmaceutically acceptable carrier, wherein the pH of the composition is about 6 or higher, the composition comprises less than about 200 mg/ml cyclodextrin, and at least about 50% of the midazolam is present in solution. Uses of these compositions are also disclosed.

36 Claims, 6 Drawing Sheets

RAPID ONSET LIQUID MIDAZOLAM COMPOSITION FOR BUCCAL ADMINISTRATION

RELATED APPLICATIONS

This application claims priority to GB Application Ser. No. GB1010453.7, filed Jun. 22, 2010, the contents of which are hereby incorporated herein by reference in their entirety.

BACKGROUND

This invention relates to a pharmaceutical composition. In particular, it relates to an improved liquid pharmaceutical composition suitable for the treatment of epilepsy. It further relates to a liquid pharmaceutical composition suitable for use as an anaesthetic.

Midazolam, i.e. 8-chloro-6-(2-fluorophenyl)-1-methyl-4H-imidazo[1,5-a][1,4] is a diazepine of the formula:

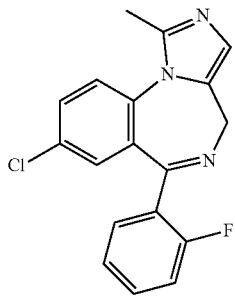 [SMILES: Cc1ncc2n1-c1ccc(Cl)cc1C(c1ccccc1F)=NC2]

Is a well-documented product with sedative, anxiolytic, amnesic and hypnotic properties. It is commercially available in the form of its hydrochloride, for example in the form of a glycerine-based syrup sold under the trade name VERSED®, which contains 2.5 mg/ml of midazolam. It is also sold in the form of its maleate salt, for example in tablets containing 7.5 mg or 15 mg per tablet under the trade mark DORMICUM®. A product which is formulated for administration via the buccal route is EPISTATUS®. Buccal formulations of midazolam are also disclosed in EP1323422.

It is known that midazolam can exist in solution both in a closed ring form and also in an open ring form. These two forms are in equilibrium with one another:

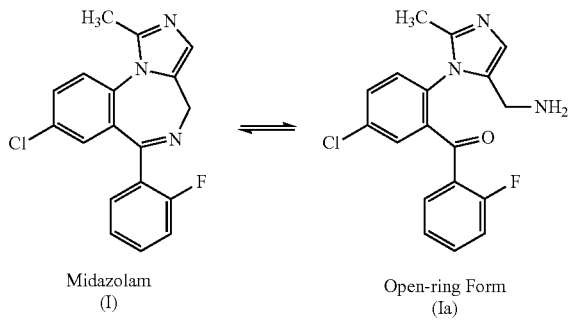 [SMILES: Cc1ncc2n1-c1ccc(Cl)cc1C(c1ccccc1F)=NC2 ; Cc1ncc(CN)n1-c1ccc(Cl)cc1C(=O)c1ccccc1F]

Midazolam (I)     Open-ring Form (Ia)

The amount of the open ring form (Ia) present in aqueous solution is influenced by pH. A chart showing the effect of pH on the proportion of midazolam present in the open ring form is provided as FIG. 1.

One of the factors determining the rate of physiological absorbtion of midazolam is the proportion of open ring (Ia) midazolam present in the formulation. The closed ring form (I) of midazolam is lipophilic and is more rapidly absorbed than the open ring form (Ia). It is therefore desirable to provide a formulation in which the majority of midazolam is present in the closed ring form (I).

While attempts to develop therapeutically effective higher pH formulations of midazolam have been made, these have been unsuccessful due to the inverse relationship between pH and the solubility of midazolam. For example, Olivier et al, International Journal of Pharmaceutics, 2001 (213), pages 187 to 192, concluded the satisfactory solubilisation of midazolam at higher pHs was a problem that remained to be solved.

At pH 8, the solubility of midazolam is just 0.055 mg/ml in aqueous solution. To deliver a therapeutically effective amount of such a solution, the volume required would be unacceptably large.

WO01/30391 provides an example of an attempt to formulate midazolam at a higher pH while circumventing the problem of reduced solubility. This is achieved by the use of cyclodextrin, which forms an inclusion complex with midazolam, retaining it in solution. However, the release of midazolam from cyclodextrin complexes is slow and this increases the time lag between administration and the onset of therapeutic effect.

As a result of the low solubility of midazolam at higher pHs, commercially available liquid formulations of midazolam tend to have pHs of no greater than about 5 as at these pHs, there is a sufficiently high proportion of midazolam in the closed ring form to ensure an acceptable degree of efficacy, while the solubility of midazolam is sufficient to enable a relatively low volume of carrier liquid to be used.

For example, in a typical syrup for oral administration, e.g. VERSED® syrup, the pH ranges from 2.8 to 3.6. Within that range, the solution may contain up to about 40% of midazolam in the open ring form (Ia). Following administration, the medicament will become exposed to physiologic conditions, including pHs in the range of 5 to 8, and will be absorbed into systemic circulation under those conditions. Thus, the majority of the midazolam present in the open-ring form present in the medicament will be converted to the closed ring form upon absorbtion. However, this change of pH and absorbance of midazolam will not occur immediately, upon administration, and there is a time lag between administration and the onset of therapeutic activity of approximately 10 to 30 minutes.

The buccally administered form of midazolam, EPISTATUS® is an extremely convenient and straightforward vehicle for delivering midazolam rapidly to patients suffering from epileptic seizures or significant amounts of pain. The pH of the EPISTATUS® product is around 4.5 to 5.5 and the proportion of midazolam in the open ring form (Ia) is approximately 1%.

The rate of absorbtion of midazolam from the EPISTATUS® formulation is sufficiently high to provide a rapid onset of therapeutic effect in patients. However, in view of the importance of the rapid delivery of midazolam to patients in need thereof, it would nevertheless be advantageous if the rate of absorbtion could be improved.

This is because epileptic seizures are a common cause of neurological medical emergency and may result in brain damage. Failure to relieve the symptoms of an epileptic seizure in less than about 15 minutes may lead to death. Accordingly, it is extremely desirable to treat a patient suffering from an epileptic seizure as promptly as possible so as to minimise the risk of brain damage or death to the patient. Additionally, when used as an anaesthetic, it is desirable, for obvious reasons, to treat a patient suffering from pain as promptly as possible.

The use of injectable formulations of midazolam is common. While midazolam administered in this way will have a rapid onset of therapeutic effect, it will not be suitable for use in all patient groups. For example, the use of a needled syringe with a patient suffering from an epileptic seizure will be problematic and potentially dangerous to both the patient and the healthcare professional administering the medicament. Additionally, the use of needled syringes is likely to raise anxiety in certain patient groups, such as children.

Accordingly, the administration of midazolam via the mucous membranes of a patient is a desirable route of administration for midazolam. Administration via this route offers the advantages of rapid therapeutic onset as well as the avoidance of needled syringes. Administration of midazolam via the buccal, nasal, rectal and/or sub-lingual mucous membranes is especially desirable.

Attempts to prepare formulations of midazolam for nasal administration have been made, for example, as reported by Wilton et al., Anesthesiology 1988, 69, pages 972-5. Most studies on intranasal formulations of midazolam have made use of a dilute aqueous midazolam injection solution that is not suitable for nasal administration because of a low pH (3 or less) which causes intense discomfort to patients and also because they are prone to nasal run-off.

Attempts have been made to overcome these problems. For example, Wermeling et al., Anasthesia & Analgesia, August 2006, volume 103 number 2, pages 344-349, developed a formulation containing midazolam, polyethylene glycol 400, butylated hydroxytoluene, saccharin and propylene glycol. That formulation provided 2.5 mg of midazolam in a 0.1 mL spray delivered using a modified version of a commercially available unit-dose spray pump. However, the formulation was associated with numerous adverse events, including eye watering (58% of doses), dizziness (17% of doses), bad taste (25% of doses), and nasal congestion/feeling nasopharyngeal irritation (100% of doses).

There is accordingly a need to provide an improved formulation for the administration of midazolam to the mucosal membranes of a patient in need thereof, e.g. a patient suffering an epileptic seizure, or suffering from unacceptable levels of pain.

SUMMARY OF INVENTION

The present invention seeks to provide a liquid medicament which provides a more rapid onset of therapeutic effect than midazolam-containing formulations of the prior art, that does not raise anxiety levels in patients, which can safely be used with patients suffering from epileptic seizures, which is stable, and/or which can be administered to the mucous membranes of patients without causing discomfort.

According to a first aspect of the present invention there is provided a liquid composition for administration to a patient comprising midazolam and a pharmaceutically acceptable carrier, the composition having a pH of about 6 or higher, the viscosity of the composition being 200 to 400 CP, the formulation comprising less than 200 mg/ml cyclodextrin, and at least 50% of the midazolam being present in solution.

The formulations are suitable for administration to patients via any mucosal membrane. In preferred embodiments, the formulations are suitable for buccal, nasal, rectal and/or sub-lingual administration.

DETAILED DESCRIPTION OF EMBODIMENTS

Figure 1:
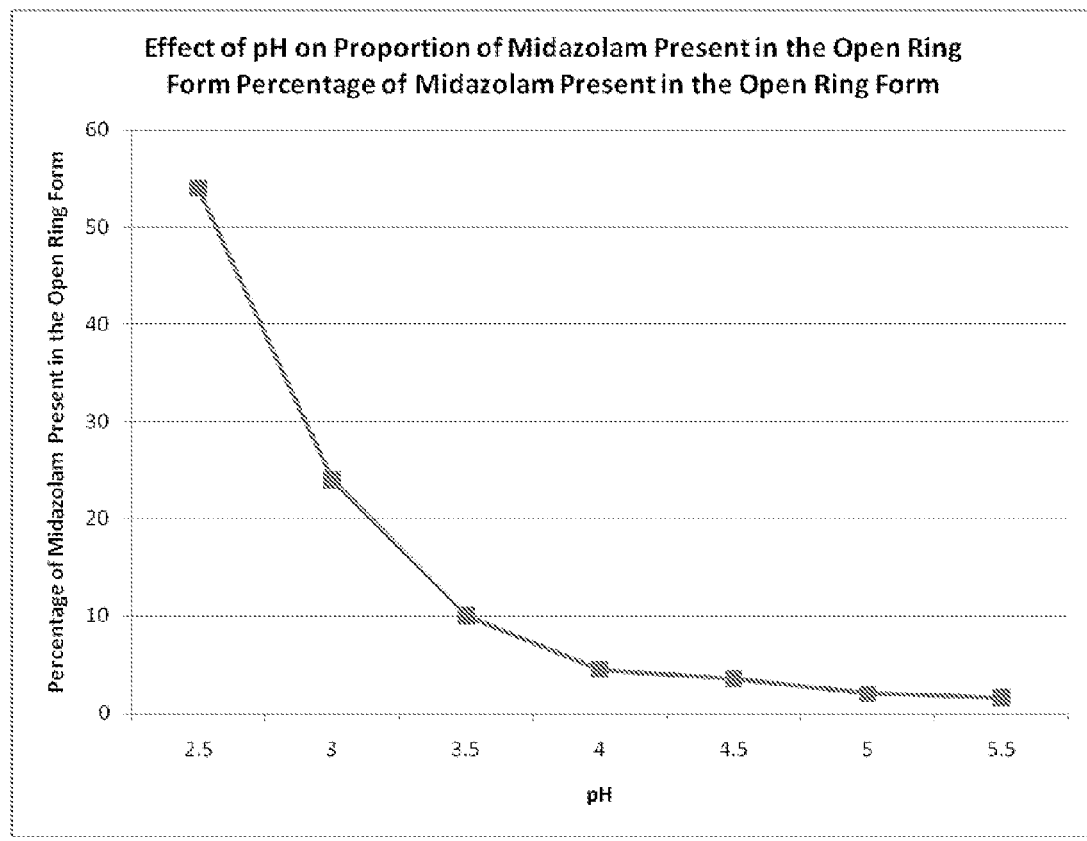
FIG. 1 is a chart showing an effect of pH on the proportion of midazolam present in an open ring form.

The possibility of raising the pH of liquid formulations comprising midazolam (and thus the proportion of the lipophilic closed ring form of midazolam) has previously been limited by a simultaneous reduction in solubility of that active. It has surprisingly been found that when the higher pH formulations of the present invention are employed, midazolam is highly, if not totally, soluble. More specifically, in those formulations, at least about 50% of midazolam is retained in solution. In preferred embodiments of the present invention, at least about 60%, 70%, 80%, 90%, 95%, 98% or 99% of midazolam is retained in solution. In especially preferred embodiments, substantially all of the midazolam present is retained in solution.

This is achieved without the need for the use of substantial amounts of cyclodextrin. Although cyclodextrin does aid the solubility of midazolam at higher pHs, it will form inclusion complexes and the release of midazolam from those complexes upon administration will delay the onset of the therapeutic effect. Thus, the formulations of the present invention include less than 200 mg/ml of cyclodextrin. The formulations preferably include less than 150 mg/ml, 100 mg/ml, 50 mg/ml, 25 mg/ml, 10 mg/ml, 5 mg/ml, or 2 mg/ml of cyclodextrin. In especially preferred embodiments of the present invention, the formulations contain less than 1 mg/ml of cyclodextrin or are substantially free of cyclodextrin.

The onset of therapeutic effect of the compositions of the present invention will clearly depend on the rate of their passage across the mucosal membrane. Advantageously, the formulations of the present invention are capable of doing so more rapidly than lower pH counterpart compositions. Thus, in preferred aspects of the present invention, the formulations of the present invention exhibit a flux rate of about 20 $\mu g/cm^2$/hour or greater, about 30 $\mu g/cm^2$/hour or greater, about 40 $\mu g/cm^2$/hour or greater, about 50 $\mu g/cm^2$/hour or greater, about 60 $\mu g/cm^2$/hour or greater, about 70 $\mu g/cm^2$/hour or greater or about 80 $\mu g/cm^2$/hour or greater.

For the purposes of the present invention, flux rate is measured at 21° C. with an infinite dose of active using a Franz cell (e.g. Rotulex No. 18) with a 250 $\mu m$ membrane and a UV-visible spectrophotometer (Spectronic Biomate, Thermo Electron Limited, Cambridge, UK).

Although the rates of flux measured using this apparatus are not directly comparable with in-vivo flux rates, this system does enable the consistent measurement of flux under conditions which mimic biological conditions.

By providing midazolam in a solution, the drawbacks associated with the use of other types of liquid medicament systems, such as emulsions or true suspensions (i.e. those where greater than 50% of medicament is suspended therein) can be avoided. More specifically emulsions are known to be prone to stability problems, especially when stored over extended periods of time as the oil and aqueous phases may separate out into a bilayered system. Additionally, when suspensions are stored for prolonged periods, the suspended material may settle and agglomerate, making its delivery difficult.

The proportion of midazolam in the closed ring form (I) in the advantageous formulations of the present formulation is at least 99%. More preferably, the proportion of midazolam in the closed ring form (I) is at least 98%, at least 99%, at least 99.5%, at least 99.7% or even at least 99.9%.

In prior art formulations having a pH of 4 to 5, approximately 95 to 98% of midazolam was present in the closed ring form. While the therapeutic activity of those medicaments could hypothetically be improved by increasing the pH, and thus the proportion of the closed ring structure present from 95 to 98% to at least 99%, this increase in clinical effect is not justified when weighed against the difficulty of formulating midazolam at higher pHs.

The formulations of the present invention advantageously retain at least 50% of midazolam in solution with the vast majority of the active present in the closed ring form. In addition to improving the efficacy and the speed of onset of therapeutic effect, a further advantage exhibited by those formulations is an improvement in stability.

More specifically, it has been observed that conventional formulations comprising midazolam include certain impurities, which become more prevalent upon extended storage of those products.

Figures 2A, 2B, 2C, 2D:
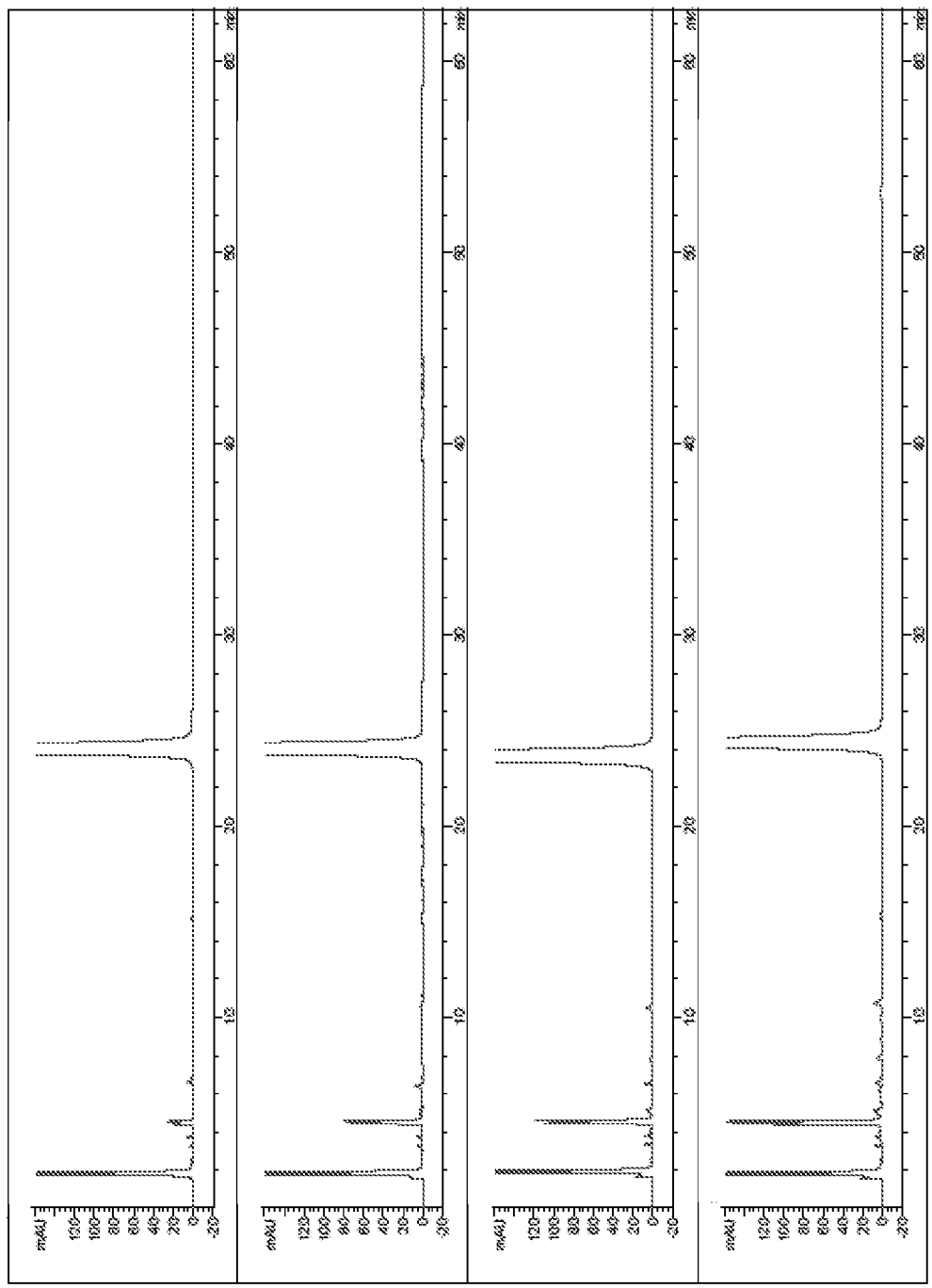
FIGS. 2A-2D are graphs showing HPLC traces over time in formulations of midazolam.

HPLC traces which confirm the gradual increase of addition products present in prior art formulations of midazolam over time are provided as FIGS. 2A to 2D. Those traces were obtained from samples of Epistatus which were stored under accelerated conditions (40° C. and 75% relative humidity) and tested after 1 month (FIG. 2A), 3 months (FIG. 2B), 6 months (FIG. 2C) and 9 months (FIG. 2D).

The broad peak at approximately 24 minutes in all four traces is provided by midazolam. The double peak at approximately 4.5 minutes is provided by two compounds, 3-carboxy-2-(8-chloro-1,6-dimethyl-4H-imidazo[1,5-a][1,4]benzodiazepin-2-ium-2-yl)propanoate and 3-carboxy-3-(8-chloro-1,6-dimethyl-4H-imidazo[1,5-a][1,4]benzodiazepin-2-ium-2-yl)propanoate, or, for brevity, SMA and SMB. The intensity of that double peak increased over time. While the increase in the amounts of the impurities present was not of sufficient magnitude to contravene the purity and efficacy requirements placed on the Epistatus product, they are nevertheless undesirable.

It has been surprisingly been found that, by formulating midazolam at higher pHs, the amounts of impurities present, especially SMA and SMB, have been significantly reduced.

Without wishing to be bound by theory, it is believed that this advantageous reduction of the amount of impurities is connected to a reduction or elimination of the amount of midazolam present in the open ring form. More specifically, the open ring form of midazolam provides reaction sites at which additive reactions can take place, for example, with counterions from the midazolam salt used to prepare the Epistatus formulation.

Thus, if midazolam is included in a formulation in the form of, for example, its maleate salt, the resultant maleic acid present in solution can degrade the open ring form of midazolam to form succinyl derivatives, such as SMA and SMB. It is envisaged that counterions other than maleate which are used to form salts with midazolam will be involved in analogous unwanted reactions with the open ring form of midazolam.

Initially, there will only be a very small proportion of these derivatives formed, due to the low proportion of the open ring form of midazolam which is present. However, as midazolam in the open ring form is converted to the addition salts mentioned above, this will drive the dynamic equilibrium between the open and closed forms of midazolam to form additional quantities (albeit low) of the open ring form of midazolam which will in turn be converted to form further quantities of the unwanted degradants. It will be appreciated that over time, this effect will cause the proportion of these addition products to increase, while decreasing the amount of midazolam present. It is believed that by maintaining a negligible amount of midazolam in the open ring form, the formation of impurities is reduced.

In preferred embodiments of the present invention, the pH is at least about 7.0, 7.5 or 8.0. In especially preferred embodiments, the pH falls within the range of about 8 to about 11.0, about 8 to about 10.5 or most preferably about 8 to about 10.

A further advantage of the use of higher pH formulations of midazolam is that they are more suitable for nasal and buccal administration than prior art, low-pH formulations. Those acidic prior art formulations, when administered nasally, cause discomfort as the acidic medicament acts as an irritant to the nasal mucosa, causing stinging of the nasal membrane. Further, the use of formulations having a pH of 3 or less via the buccal route will be damaging to buccal mucosa and also to dental enamel. These problems are avoided through the use of the formulations of the present invention.

Excessively high pHs, for example, above 11.0 are generally avoided as the rate of degradation of midazolam is increased and also because formulations at such high pHs will have an unacceptable 'soapy' taste.

The pH of the formulation may be inherently provided by the excipients present in the formulation or a pH adjustment agent may be employed. The pH adjustment agent may comprise a simple base or acid, or may additionally or alternatively comprise a buffer.

The use of a buffer is preferred as, once the formulation is administered to the mucous membranes, especially those in the buccal cavity, the buffer will maintain the desired pH of the formulation whereas the pH of a simple basified formulation will be adjusted to a mildly acidic pH by saliva once administered. Any pharmaceutically acceptable buffer may be employed, although buffers which maintain the pH of the formulation at a basic pH are preferred. Examples of such buffers include phosphate buffers, glycine/NaOH buffers, carbonate or bicarbonate buffers.

The compositions of the present invention preferably comprise about 5 mg/ml to about 100 mg/ml of midazolam. In preferred embodiments, the compositions comprise about 5 to 80 mg/ml, about 5 to 60 mg/ml, 5 to 30 mg/ml, 5 to 20 mg/ml, 6 mg/ml to about 15 mg/ml or most preferably from about 7.5 mg/ml to about 12.5 mg/ml of midazolam.

The compositions of the present invention preferably have a viscosity of about 500 CP or lower when measured at 22° C. In preferred embodiments, the viscosity may be about 200 to 400 CP, about 250 CP to 350 CP, or most preferably, about 270 CP to 330 CP.

Viscosity may be measured using any apparatus known to those skilled in the art, for example, Brookfield LVDV +/−.

The use of a formulation having a viscosity of from about 200 CP to about 400 CP is advantageous as when it is administered to the mucous membranes of a patient, the liquid will be less mobile and will remain localised in the desired position while midazolam is absorbed. For example, if the compositions are administered into the buccal cavity of a patient, there is a low degree of circulation of the formulation throughout the mouth, meaning that the risk of a quantity of the formulation trickling down the patient's throat is minimised, if not eliminated.

The viscosity of the formulation may inherently be provided by the other excipients included therein, or a viscosity enhancing component may additionally be present. Preferred viscosity enhancing components include glycerol, carrageen, quince seed, casein, dextrin, gelatin, carboxy vinyl polymer, hydrogenated starch hydrolysate, maltitol syrup, sugar (dextrose, glucose and sucrose), cellulose derivatives such as sodium or calcium carboxymethylcellulose, hydroxy ethyl cellulose and hydroxypropyl cellulose, a polysaccharide, a pectin, agar, a hydrophilic gum such as acacia gum, guar gum, arabic gum and xanthan gum, tragacanth gum, alginic acid, an alginate, dextran, a carbomer resin or mixtures thereof.

To increase shelf-life, the formulation may include a microbial preservative. Any preservative which does not adversely interact with midazolam or any of the excipients may be employed. Preferred preservatives include alcohol, benzalkonium chloride, benzethonium chloride, benzoic acid, benzyl alcohol, bronopol, butyl-paraben, cetrimide, chlorhexidine, chlorobutanol, chlorocresol, cresol, ethanol, ethylparaben, glycerin, imidurea, methylparaben, phenol, phenoxyethanol, phenylethyl alcohol, phenyl mercuric acetate, phenyl mercuric borate, phenylmercuric nitrate, potassium sorbate, propylene glycol, propyl-paraben, sodium benzoate, sodium propionate, sorbic acid and thiomersal or a mixture thereof. The amount of preservative may range, for example, from about 0.5 to about 10 mg/ml of the composition, preferably from about 1 to about 5 mg/ml of the formulation.

Shelf life may also be increased by preventing the oxidation of midazolam. This may be achieved by limiting exposure of the formulation to light. For example, if the formulation of the present invention is provided as a bulk solution, it would be preferable for that solution to be packaged in a dark-coloured glass bottle. Alternatively, if the formulation is to be provided in unit dosage form, then the dosage forms are preferably overwrapped with an opaque packaging material.

Additionally, antioxidants, such as sodium metabisulphite, ascorbic acid, or chelating agents, such as sodium edetate, may be employed. Glycerine may also be used to act as a stabilising agent. The amount of antioxidant and stabilising agent may range, for example, from about 0.5 to about 10 mg/ml of the composition, preferably from about 1 to about 5 mg/ml of the formulation.

The formulation may also contain an antifungal agent. Typical antifungal agents include alkali metal salts of an alkyl hydroxybenzoate, such as sodium methyl hydroxybenzoate, sodium propyl hydroxybenzoate, or mixtures thereof. The amount of antifungal agent may range for example, from about 0.5 to about 1 mg/ml of the composition, preferably from about 1 to about 5 mg/ml of the formulation.

A sweetening agent may be employed in the formulations of the present invention. Preferred sweetening agents include sugar, acesulfame, sucralose, high fructose corn syrup, maltitol syrup, cyclamates, saccharins and aspartame. However, in the case of formulations intended for administration via the buccal cavity, as the formulation will be held in the buccal cavity, adjacent to the teeth, the sweetening agent is preferably a synthetic sweetening agent.

A flavour enhancer may also be employed in the formulations of the present invention. The flavour enhancer may impart any flavour to the formulations which improves their acceptance by patients. Preferred flavours include strawberry, raspberry, cranberry, banana, peach, mango, passion fruit, apple, grape, caramel, watermelon, chocolate, coffee, yoghurt, vanilla, ice cream or bubblegum.

The amount of sweetening agent and/or flavour enhancer preferably ranges from about 10 mg/ml to about 100 mg/ml of the formulation.

Any pharmaceutically acceptable carrier which is capable of retaining midazolam in solution at higher pHs may be included in the formulation of the present application. The carrier is preferably one which is miscible with water. The carrier may comprise alcohols (including lower molecular weight alcohols e.g., ethanol and polyhydric alcohols, e.g., glycerine, glycerol, glycerol tri-esters with carboxylic acids having 1 to 6 carbon atoms, maltitol, non-toxic glycols such as polyethylene glycol or propylene glycol, especially propylene glycol 200 to 400) and their derivatives, and oils (e.g., fractionated coconut oil and arachis oil) or mixtures thereof. In preferred arrangements of the present invention, the carrier is present in an amount which retains midazolam in solution at a pH greater than 6. Around 5 to 75, 15 to 60, or 25 to 50 percent carrier may be employed in preferred embodiments of the present invention.

In especially preferred embodiments, the carrier system comprises glycerol and/or a glycol (preferably either or both of polyethylene glycol and/or propylene glycol) and optionally other excipients such as water, maltitol or any of the other potential carriers outlined above. In such a carrier system, the weight ratio of glycerol:glycol preferably ranges from about 0:100, about 1:99, about 10:90, about 15:85, or about 20:80 to about 50:50, to about 45:55, or to about 40:60.

According to a further aspect of the present invention, there is provided a liquid composition for administration to a patient comprising midazolam and a pharmaceutically acceptable carrier, the composition comprising less than about 200 mg/ml cyclodextrin, the carrier comprising a glycol and optionally glycerol, wherein the weight ratio of glycerol:glycol ranges from about 0:100 to about 50:50 and at least about 50% of the midazolam is present in solution.

The compositions of this aspect of the present invention may be used in the treatment of epilepsy or in inducing anaesthesia.

In the compositions of the present invention, the amount of ethanol present is preferably less than about 30%, less than about 25%, less than about 20%, less than about 15%, less than 10%, less than 5%, or less than 1%, all by weight of the composition. In certain embodiments, the compositions of the present invention are essentially free of ethanol.

Any pharmaceutically acceptable and effective form of midazolam may be included in the formulations of the present invention. For example, the free molecule of midazolam may be employed. Alternatively, a salt may be used. In preferred embodiments of the present invention, the hydrochloride, maleate, sulphate, tartrate, acetate, or citrate salt is used. The hydrochloride and maleate salts are the the most commonly used forms of midazolam. Additional pharmaceutically acceptable salts include, but are not limited to, hydrochloride, hydrobromide, hydroiodide, nitrate, sulphate, besylate, bisulphate, phosphate, acid phosphate, propionate, isonicotinate, acetate, lactate, salicylate, citrate, tartrate, pantothenate, bicarbonate, bitartrate, ascorbate, succinate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

The formulations of the present invention may be administered sequentially or simultaneously with other therapeutic agents selected from (but not limited to) corticosteroids, cytotoxics, antibiotics, immunosupressants, nonsteroidal antiinflammatory drug, other narcotic analgesics, local anaesthetics, NMDA antagonists, neuroleptics, anticonvulsants, antispasmodics, antiemetics, antidepressants or muscle relaxants. The agents can be administered separately or in combination.

The formulations of the present invention may be provided as a bulk solution, from which doses can be removed. However, in a preferred embodiment, the formulation is provided as a unit dose. The unit dose is preferably provided in a single-use means of administration, most preferably a dropper, such as that disclosed in UK Patent Application No. 0922357.9, the contents of which are incorporated by reference.

The unit dose may comprise between about 0.1 to about 20 ml of medicament. In more preferred embodiments, the unit dose comprises about 0.2 to about 10 ml, about 0.25 to about 5 ml, or more preferably, about 0.5 to about 2 ml of the formulation. In a most preferred arrangement, the unit dose comprises 1 ml of medicament. The use of a unit dose of medicament is advantageous as the risk of administering an incorrect dose is eliminated.

Compositions of this aspect of the present invention include midazolam as the principle active agent. However, analogous compositions may be used to formulate alternative active ingredients in place of or in addition to midazolam, for example benzodiazepines, including alprazolam, bretazenil, bromazepam, brotizolam, chlordiazepoxide, cinolazepam, clonazepam, clorazepate, cloxazolam, delorazepam, diazepam, estazolam, etizolam, etizolam, flunitrazepam, flurazepam, flutoprazepam, halazepram, ketazolam, loprazolam, lorazepam, lormetazepam, medazepam, nimetazepam, nitrazepam, nordazepam, oxazepam, phenazepam, pinazepam, prazepam, premazepam, quazepam, temazepam, tetrazepam and triozolam.

Alternative active ingredients which may be formulated in the compositions of the present invention in place of or in addition to midazolam include nicotine and derivatives thereof and/or opioids, including codeine, morphine, diacetylmorphine, dihydrocodeine, hydrocodone, oxycodone, hydromorphone, nicomorphone, oxymorphone, fentanyl, methylfentanyl, alfentanil, sufentanil, remifentanil, pethidine, methadone, buprenorphine, tramadol.

The formulation of the present invention may be provided as part of a kit. The kit may also comprise instructions to administer the formulation to the buccal, nasal, sub-lingual and/or rectal cavity of a patient in need thereof. The formulation is preferably included in the kit in the form of at least one unit dose of the formulation of the present invention. The kit may also comprise one or more doses of a further therapeutic agent.

According to a third aspect of the present invention, there is provided the use of midazolam in the manufacture of a liquid medicament having a pH of about 6.0 or greater and comprising less than 200 mg/ml cyclodextrin for administration to a patient to treat epileptic seizures and/or induce a degree of anaesthesia in the patient, wherein at least 50% of the midazolam is present in solution.

According to a fourth aspect of the present invention, there is provided the use of midazolam to treat epileptic seizures and/or induce a degree of anasthesia, wherein the midazolam is administered as a liquid medicament having a pH of about 6.0 or higher and comprising less than 200 mg/ml of cyclodextrin to a patient, and at least 50% of the midazolam is present in solution.

According to a fifth aspect of the present invention, there is provided a method of treating epileptic seizures and/or inducing a degree of anaesthesia in a patient by administering the formulations discussed above to a patient.

In these third, fourth and fifth aspects of the present invention, the midazolam is preferably administered in the formulations described above.

The formulations of the present invention are suitable for use with all patient groups. However, certain advantages are especially apparent when the formulations are used with paediatric patients. For example, administration of midazolam via the buccal route avoids causing anxiety to patients through the use of a needled syringe, which will be especially acute for such younger patients. Additionally, the use of formulations having acceptable flavour profiles will be especially important for such patients.

The term 'paediatric patient' covers all children and adolescents below the age of 18. The formulations of the present invention are especially suitable for younger patients, e.g. pre-term infants to children of 12 to 14 years of age.

For the avoidance of any doubt, where the concentration of midazolam is provided, e.g. the formulation has a concentration of 5 mg/ml of midazolam, it is the concentration of free midazolam which is provided and not the concentration of any salt of midazolam that may be employed unless otherwise specified.

Where reference is made to the proportion of the open or closed ring forms of midazolam, e.g. the proportion of the closed ring form present is 99%, the percentage given is a proportion of the total amount of midazolam present.

Where 'mg/ml' units are used to define the concentrations of midazolam and excipients, the concentrations are provided as a proportion of the total formulation.

The invention is further illustrated in the following Examples.

Example 1

A range of formulations were prepared which had the following composition:

| Material | Amount | |
|---|---|---|
| Midazolam Maleate | 13.60 | mg (equivalent to 10.00 mg midazolam) |
| Saccharin Sodium | 40.00 | mg |
| Purified Water | 0.06 | ml |
| Ethanol | 197.250 | mg |
| Glycerol | 220.500 | mg |
| Lycasin$^{RTM}$ 80/55 | To 1.0 | ml |
| Sodium Hydroxide | QS to appropriate pH | |

The formulations had pHs of 3.4, 4.1, 4.8, 5.5, 6.2, 6.9, 7.5, 8.0, 8.5, 9.0, 10.0. Once prepared, the formulations were stored at 40° C. and at a relative humidity of 75%. After one month of storage, the impurity profile of the samples was measured and the following results were observed:

| pH of Formulation | Amount of SMA (%) | Amount of SMB (%) | Total Impurities (%) |
|---|---|---|---|
| 3.4 | 0.54 | 0.61 | 2.12 |
| 4.1 | 0.62 | 0.71 | 1.70 |

-continued

| pH of Formulation | Amount of SMA (%) | Amount of SMB (%) | Total Impurities (%) |
|---|---|---|---|
| 4.8 | 0.61 | 0.70 | 1.56 |
| 5.5 | 0.56 | 0.64 | 1.45 |
| 6.2 | 0.49 | 0.57 | 1.31 |
| 6.9 | 0.37 | 0.42 | 1.04 |
| 7.5 | 0.19 | 0.33 | 0.91 |
| 8.0 | 0.10 | 0.12 | 0.61 |
| 8.5 | 0.08 | 0.09 | 0.57 |
| 9.0 | 0.07 | 0.07 | 0.55 |
| 10.0 | 0.05 | 0.05 | 0.50 |

Figure 3:
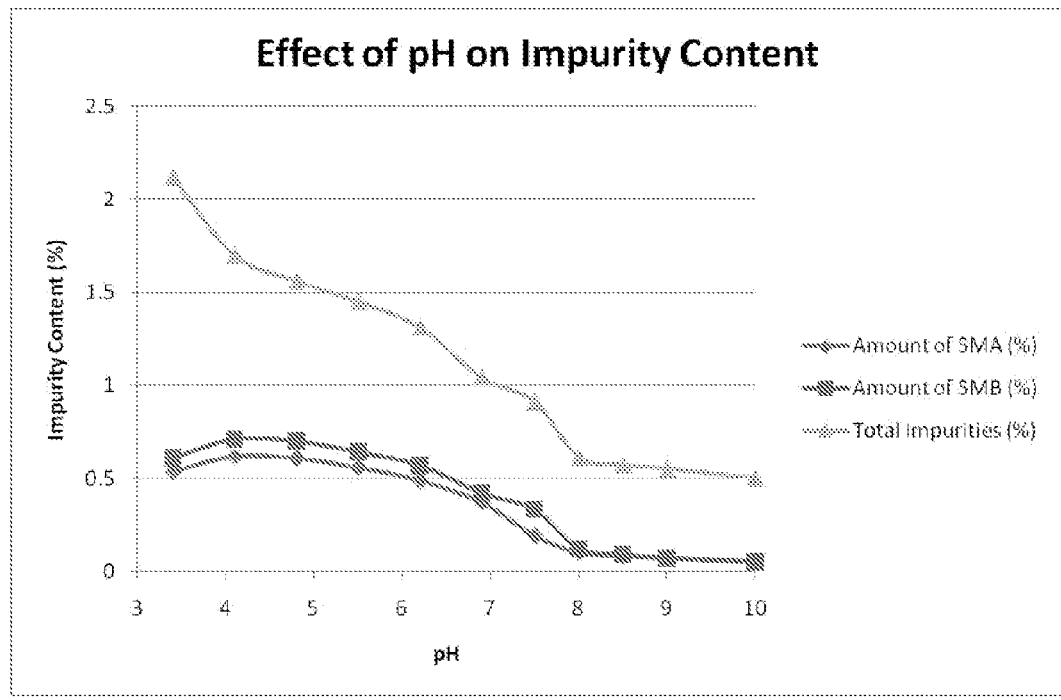
FIG. 3 is a chart showing an effect of pH on impurity content.

These results are presented on the chart provided as FIG. 3. As can be seen, formulations having increased pH benefitted from a reduction in the amount of impurities observed after storage at 40° C. and at a relative humidity of 75% relative humidity. Thus, by increasing the pH of those formulations, the stability of the midazolam in those formulations is advantageously and unexpectedly improved.

Figure 4:
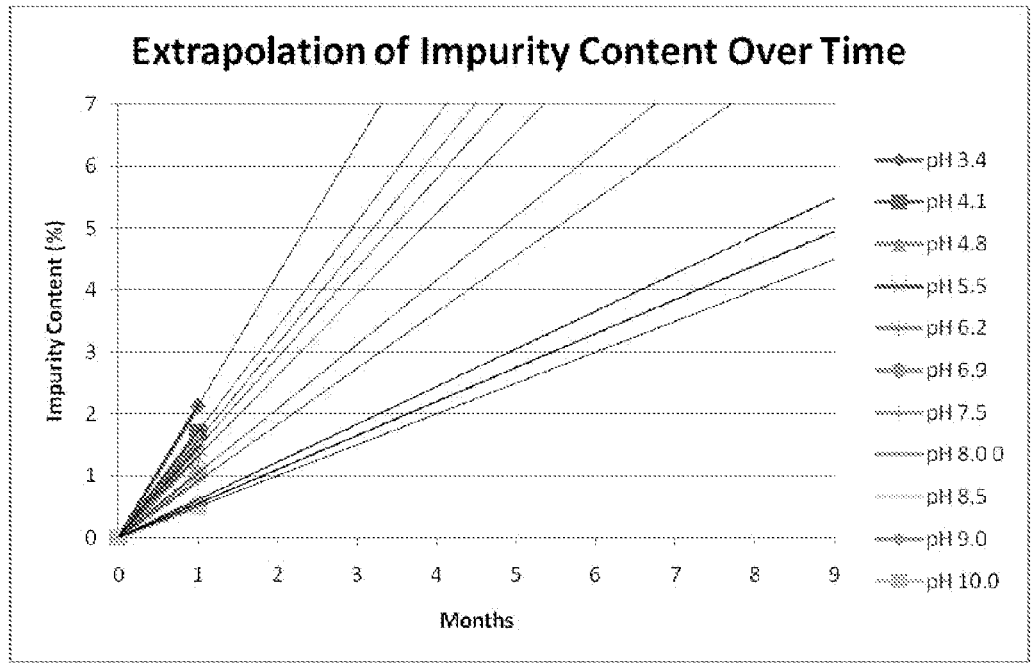
FIG. 4 is a chart showing an extrapolation of impurity content over time.

FIG. 4 is a chart showing the extrapolated impurity contents of the formulations. Assuming that the formation of the degradant by-products is relatively constant, the formulations having pHs of 8 to 10 will have an impurity content of only about 5% following storage under accelerated conditions for 9 months.

Example 2

To further investigate the effects of pH on stability, an alternative series of formulations to those discussed in Example 1 were prepared. A range of compositions comprising midazolam in solution at pH 8.5 were produced according to the following two processes:

Process 1. All of the excipients (except the 10% sodium hydroxide) were blended as a single premix, with the order of addition being water, glycerol, Lycasin®, propylene glycol/PEG 200/400, and ethanol. Once these excipients were mixed to a final homogenous solution, midazolam maleate was added.

Process 2. Midazolam maleate was firstly added to the mixture vessel. The excipients were then sequentially added in the following order: water, glycerol, Lycasin®, propylene glycol/PEG 200/400, ethanol. Midazolam was allowed to undergo boundary layer pH-induced dissolution and precipitation in the water-glycerol premix, with a ten minute delay between the addition of glycerol and Lycasin®. After addition of the remaining excipients, the vessel (a screw top glass bottle) is sealed and shaken vigorously until the solution is clear by eye, after approximately 10 to 15 minutes.

The solutions which were prepared had the compositions set out below. Also provided in the following tables is an indication of the appearance of the solutions following short term storage in a freezer, to promote crystallisation. The clarity of the obtained solutions confirm that crystallisation did not occur and that midazolam is stable therein.

Glycerol/Propylene Glycol Carrier System:

| Ingredient | Glycerol 40 (PG) 60 | Glycerol 25 (PG) 75 | Glycerol 0 (PG) 100 |
|---|---|---|---|
| | | gm/100 gm % w/w | |
| Midazolam maleate | 1.1 | 1.1 | 1.1 |
| Ethanol | 15.77 | 15.77 | 15.77 |
| Glycerol | 7.044 | 4.4025 | 0.00 |
| Propylene glycol | 10.566 | 13.2075 | 17.61 |
| Lycasin 80/85 | 57.53 | 57.53 | 57.53 |
| Deionised water | 7.99 | 7.99 | 7.99 |
| 10% sodium hydroxide in water | To pH 8.5 | To pH 8.5 | To pH 8.5 |
| Total | 100.00 | 100.00 | 100.00 |
| Appearance | Clear | Clear | Clear |

Glycerol/PEG 200 Carrier System

| Ingredient | Glycerol 40 (PEG 200) 60 | Glycerol 25 (PEG 200) 75 | Glycerol 0 (PEG 200) 100 |
|---|---|---|---|
| | | gm/100 gm % w/w | |
| Midazolam maleate | 1.1 | 1.1 | 1.1 |
| Ethanol | 15.77 | 15.77 | 15.77 |
| Glycerol | 7.044 | 4.4025 | 0.00 |
| Polyethylene glycol 200 | 10.566 | 13.2075 | 17.61 |
| Lycasin 80/85 | 57.53 | 57.53 | 57.53 |
| Deionised water | 7.99 | 7.99 | 7.99 |
| 10% sodium hydroxide in water | To pH 8.5 | To pH 8.5 | To pH 8.5 |
| Total | 100.00 | 100.00 | 100.00 |
| Appearance | Clear | Clear | Clear |

Glycerol/PEG 400 Carrier System

| Ingredient | Glycerol 40 (PEG 400) 60 | Glycerol 25 (PEG 400) 75 | Glycerol 0 (PEG 400) 100 |
|---|---|---|---|
| | | gm/100 gm % w/w | |
| Midazolam maleate | 1.1 | 1.1 | 1.1 |
| Ethanol | 15.77 | 15.77 | 15.77 |
| Glycerol | 7.044 | 4.4025 | 0.00 |
| Polyethylene glycol 400 | 10.566 | 13.2075 | 17.61 |
| Lycasin 80/85 | 57.53 | 57.53 | 57.53 |
| Deionised water | 7.99 | 7.99 | 7.99 |
| 10% sodium hydroxide in water | To pH 8.5 | To pH 8.5 | To pH 8.5 |
| Total | 100.00 | 100.00 | 100.00 |
| Appearance | Clear | Clear | Clear |

Example 3

Figure 5A:
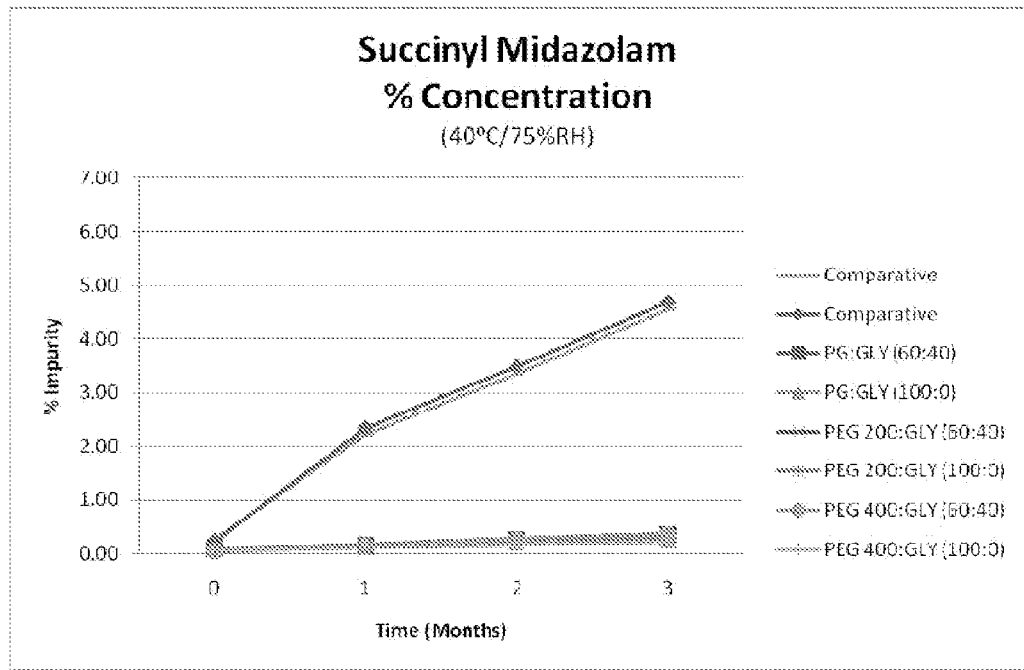
FIGS. 5A-5B are charts showing impurity percentages of tested formulations.
Figure 5B:
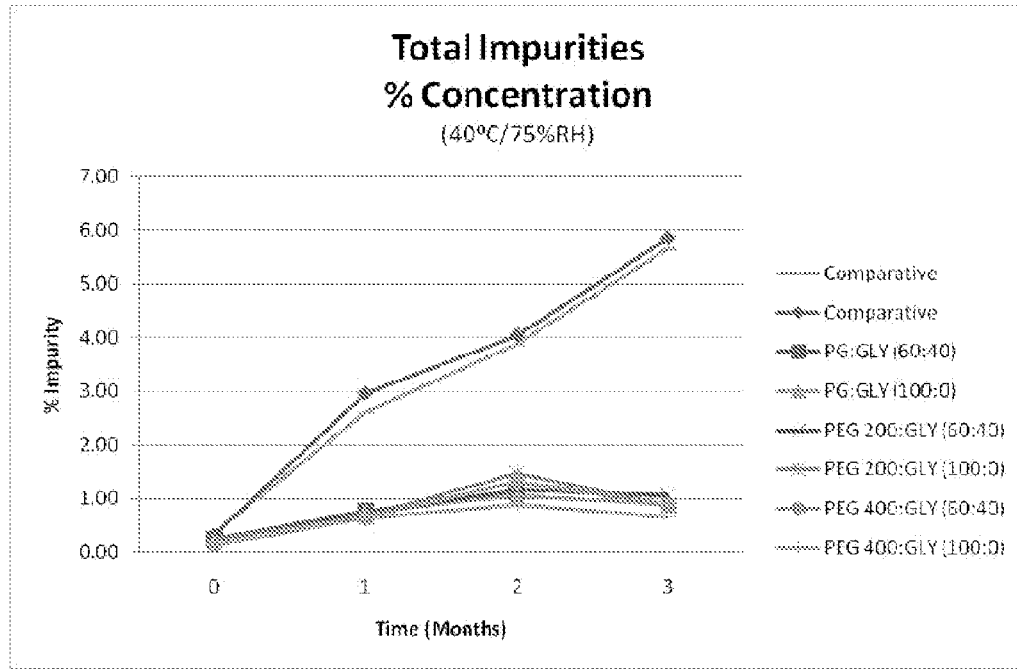

The stability of a number of the formulations discussed in Example 2 was compared against two samples of the commercially available Epistatus product (comparative) which has a pH of 4.5 to 5.5. The samples were stored for three months at a temperature of 40% and at a relative humidity of 75%. Following storage, the samples were analysed and the % concentration of succinyl midazolam (SMA, SMB) impurities and total impurities are provided as FIGS. 5A and 5B, respectively. As can be seen, the higher pH formulations of the present invention contained far lower quantities of impurities following storage for three months at a temperature of 45° C. and at a relative humidity of 75%.

The analytical method used to determine the impurity content of the formulations discussed in Example 2 differed from and had a higher level of sensitivity than the analytical method used to determine the impurity content of the formulations discussed in Example 1. Thus, the results obtained in Example 1 are not directly comparable with the results discussed in this example and illustrated in FIGS. 5A and 5B.

Example 4

The rate of flux of a composition of the present invention versus a lower pH (about 5) comparative formulation was determined using a Franz cell. Flux rate was measured at 21° C. using a Rotulex No. 18 Franz cell with an infinite dose of active and a 250 μm membrane with a UV-visible spectrophotometer (Spectronic Biomate, Thermo Electron Limited, Cambridge, UK).

The lower pH comparative formulation had the following composition:

| Material | Amount |
| --- | --- |
| Midazolam Maleate | 13.60 mg (equivalent to 10.00 mg midazolam) |
| Purified Water | 0.06 ml |
| Ethanol | 197.250 mg |
| Glycerol | 220.500 mg |
| Lycasin$^{RTM}$ 80/55 | To 1.0 ml |
| Sodium Hydroxide | QS to appropriate pH |

Figure 6:
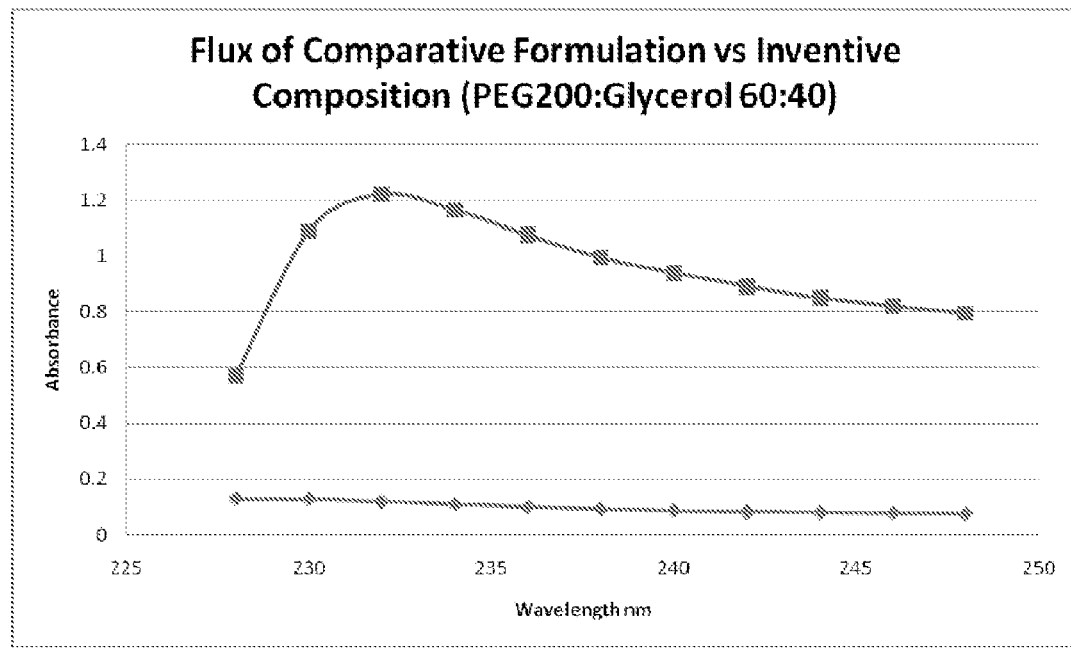
FIG. 6 is a chart showing a flux rate comparison between a comparative composition and an exemplary composition according to aspects of the invention.

The flux rate of that comparative formulation and also of the Glycerol 40:(PEG 200) 60 formulation were determined using the apparatus outlined above. The results obtained are presented graphically as FIG. 6. The upper line, with square points, are the results obtained for the inventive composition and the lower line, with diamond points, are the results obtained for the comparative composition.

As can be seen from that figure, the absorbance of the inventive composition peaked at 232 nm. The average cell volume of the comparative formulation was 2.93 ml and the average cell volume of the inventive formulation was 3.13 ml. The absorbance of 25 μg/ml standard of midazolam maleate is 1.455 at 232 nm.

Thus, the calculated flux rate of the inventive composition was 88.67 μg/cm$^2$/hour whereas the calculated flux rate of the comparative composition was only 8.12 μg/cm$^2$/hour. In other words, the inventive composition exhibited a flux rate in the Franz cell which is over ten times greater than that of the comparative composition.

This strongly suggests that the formulations of the present invention will be absorbed via the buccal cavity more rapidly than conventional compositions and thus, exhibit a faster onset of therapeutic activity.

Example 5

Additional Franz cell testing was performed using the comparative formulation discussed in Example 4 and several of the compositions prepared in Example 2.

Figure 7A:
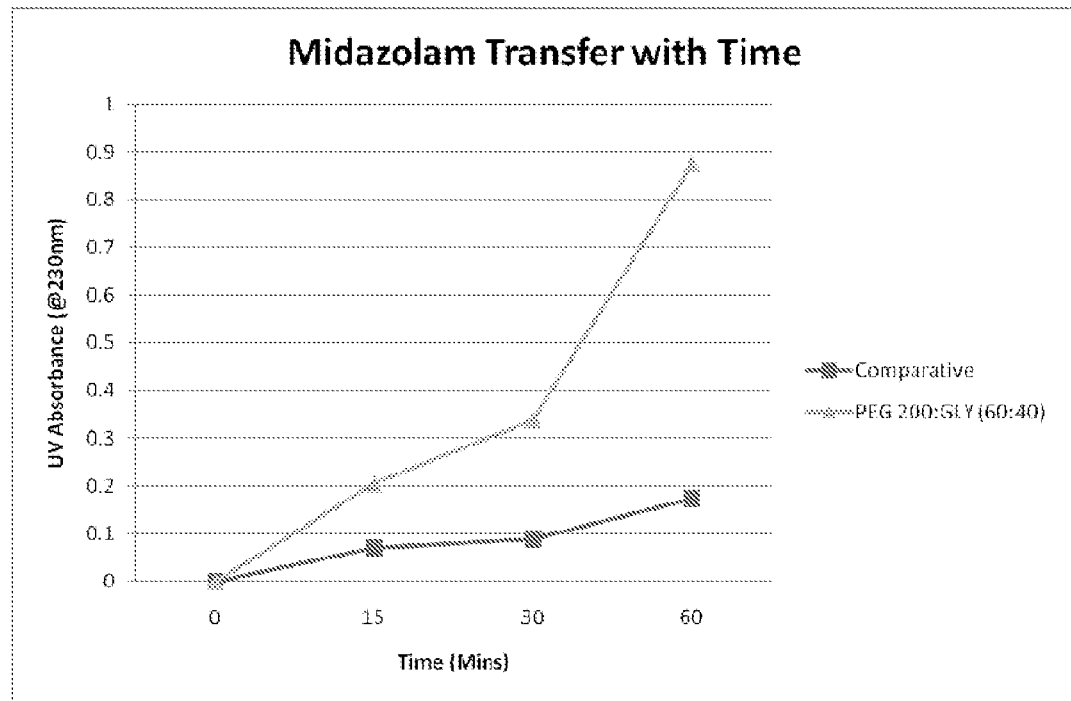
FIGS. 7A-7B are graphs showing comparisons of midazolam transfer over time between a comparative composition and exemplary compositions according to aspects of the invention.
Figure 7B:
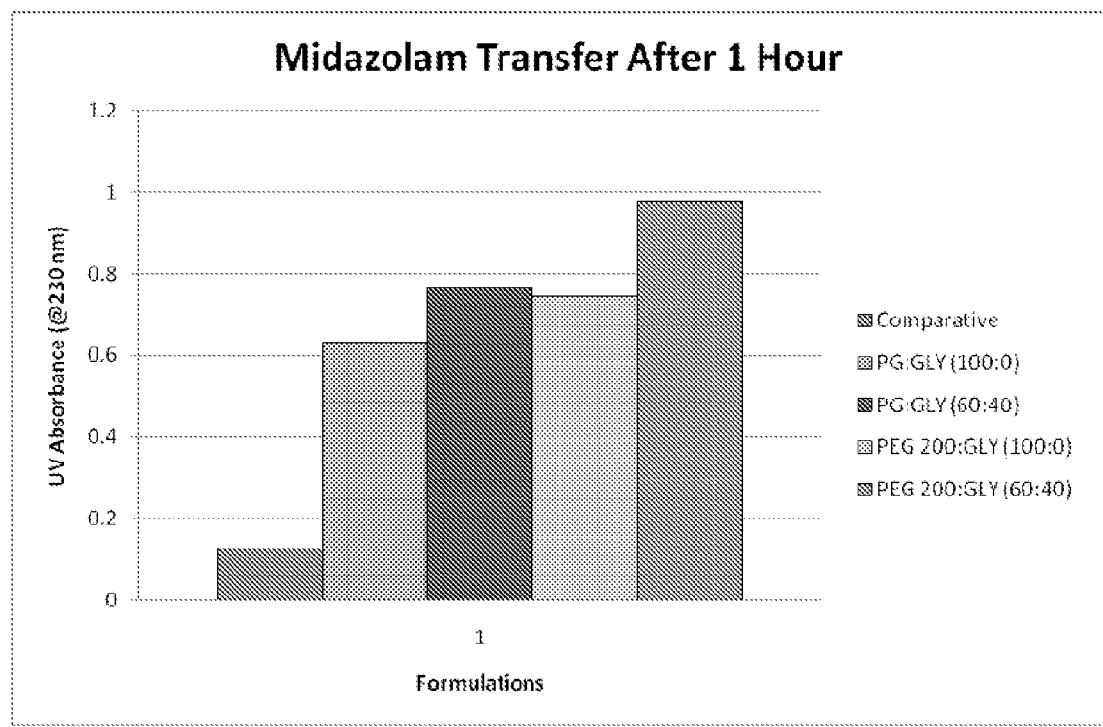

The results obtained are presented as FIGS. 7A and 7B. As can be seen from FIG. 7A, the transfer of midazolam when formulated in an inventive composition was significantly higher than the comparative formulation, and the difference between them increased as time progressed. As is clear from FIG. 7B, the advantageous results observed in FIG. 7A were not limited to the PEG 200:GLY (60:40) formulation, but were also exhibited by other formulations of the present invention.

The invention claimed is:

1. A liquid composition comprising midazolam and a pharmaceutically acceptable carrier, wherein the pH of the composition is 6 or higher, the viscosity of the composition is 200 to 400 CP at 22° C., the composition comprises less than 50 mg/mL cyclodextrin, the concentration of midazolam in the composition is 5 mg/mL to 100 mg/mL, and at least 50% of the midazolam is present in solution.

2. The liquid composition of claim 1, wherein the composition is for administration via the buccal, nasal, rectal and/or sub-lingual routes.

3. The liquid composition of claim 1, wherein the pH of the composition is 7 or higher.

4. The liquid composition of claim 1, wherein the pH of the composition is 8 or higher.

5. The liquid composition of claim 1, wherein the pH of the composition is 8 to 11.

6. The liquid composition of claim 1, wherein the pH of the composition is 8 to 10.5.

7. The liquid composition of claim 1, wherein the pH of the composition is 8 to 10.

8. The liquid composition of claim 1, wherein at least 90% of the midazolam is present in solution.

9. The liquid composition of claim 1, wherein at least 98% of the midazolam is present in solution.

10. The composition of claim 1, wherein the concentration of midazolam is 5 mg/ml to 20 mg/ml.

11. The composition of claim 1, wherein the concentration of midazolam is 6 mg/ml to 15 mg/ml.

12. The composition of claim 1, wherein the concentration of midazolam is 7.5 mg/ml to 12.5 mg/ml.

13. The composition of claim 1, wherein the viscosity of the composition is 250 CP to 350 CP at 22° C.

14. The composition of claim 1, wherein the viscosity of the composition is 270 CP to 330 CP at 22° C.

15. The composition of claim 1, wherein the composition further comprises a viscosity enhancing component.

16. The composition of claim 1, wherein the composition is free of cyclodextrin.

17. The composition of claim 1, wherein the composition further comprises a buffer.

18. The composition of claim 17, wherein the buffer is a phosphate buffer, a glycine/NaOH buffer or a carbonate or bicarbonate buffer or a mixture thereof.

19. The composition of claim 1, wherein the composition additionally comprises a sweetener, a flavour enhancer, a preservative and/or an antifungal agent.

20. The composition of claim 1, wherein the carrier comprises water, ethanol, glycerine, glycerol, polyethylene glycol, propylene glycol or mixtures thereof.

21. The composition of claim 1, further comprising an additional therapeutic agent.

22. A unit dose of the composition of claim 1.

23. The unit dose of claim 22, comprising 0.1 to 10 ml of the formulation.

24. The unit dose of claim 22, comprising 0.2 to 5 ml of the formulation.

25. The unit dose of claim 22, comprising 0.5 to 2 ml of the formulation.

26. The unit dose of claim 22, wherein the unit dose is contained within a single-use means of administration.

27. The unit dose of claim 22, wherein the single-use means of administration is a dropper.

28. A kit comprising the composition of claim 1.

29. The kit of claim 28, further comprising an additional therapeutic agent.

30. The kit of claim 29, wherein the additional therapeutic agent is provided as a unit dose.

31. The composition of claim 1, wherein the composition is for use in treating an epileptic seizure and/or inducing a degree of anaesthesia in a patient.

32. The composition of claim 31, wherein the patient is 14 years of age or under.

33. The composition of claim 31, wherein the patient is simultaneously or sequentially administered an additional therapeutic agent.

34. The composition of claim 33, wherein the composition comprises the additional therapeutic agent.

35. The composition of claim 34, wherein the additional therapeutic agent is selected from the group consisting of corticosteroids, cytotoxics, antibiotics, immunosupressants, nonsteroidal antiinflammatory drug, narcotic analgesics, local anaesthetics, NMDA antagonists, neuroleptics, anticonvulsants, antispasmodics, antiemetics, antidepressants and muscle relaxants.

36. A kit comprising the unit dose of claim 22.

* * * * *